United States Patent [19]

Belter

[11] Patent Number: 5,874,658
[45] Date of Patent: Feb. 23, 1999

[54] PURIFICATION OF ORGANIC FLUORINE COMPOUNDS

[75] Inventor: Randolph K. Belter, Zachary, La.

[73] Assignee: LaRoche Industries Inc., Atlanta, Ga.

[21] Appl. No.: 928,106

[22] Filed: Sep. 12, 1997

[51] Int. Cl.$^6$ .................................................. C07C 17/38
[52] U.S. Cl. .......................................... 570/180; 570/177
[58] Field of Search ..................................... 570/177, 180

[56] References Cited

U.S. PATENT DOCUMENTS

| | | | |
|---|---|---|---|
| 1,946,195 | 2/1934 | Davdt | 570/177 |
| 1,946,199 | 2/1934 | Dunphy | 570/177 |
| 3,873,629 | 3/1975 | Jones . | |

FOREIGN PATENT DOCUMENTS

| | | | |
|---|---|---|---|
| 1168404 | 4/1964 | Germany | 570/177 |
| 7219248 | 8/1970 | Japan | 570/177 |

Primary Examiner—Alan Siegel
Attorney, Agent, or Firm—Richard J. Hammond

[57] ABSTRACT

A method is disclosed for separating a mixture of at least one hydrofluorocarbon from hydrogen fluoride. The method comprising treating said mixture with a compound selected from the group consisting of an alkanolamine of formula $$NH_a(CH_bR_c)_d$$

where R is $C_1$ to $C_6$ linear or branched alkylene substituted with at least one hydroxy group, wherein a and d are the integers 1 or 2 and a+d=3 and b is 0 or the integer 1 or 2 and b+c=3, $C_6$ to $C_{10}$ aryl unsubstituted or substituted with halo or halo-substituted $C_1$ to $C_6$ alkyl, sulfuric acid and sulfuric acid admixed with at least one alkali metal sulfate. The hydrofluorocabon and HF form two separate phases by this treatment. The phases are readily separated.

11 Claims, No Drawings

PURIFICATION OF ORGANIC FLUORINE COMPOUNDS

FIELD OF INVENTION

This invention relates to a method for achieving phase separation of mixtures of hydrofluorocarbons and hydrogen fluoride. More particularly, this invention relates to compounds with novel properties that when added to hydrofluorocarbon/hydrogen fluoride solutions induce a phase separation and extraction.

BACKGROUND OF INVENTION

The prior art discloses that the preparation of chlorofluorocarbons, hydrofluorocarbons and hydrochlorofluorocarbons is typically carried out by reacting hydrogen fluoride with a suitable chlorocarbon or hydrochlorocarbon. See, for example U.S. Pat. No. 5,616,819.

In many cases, hydrogen fluoride can be removed by liquid/liquid phase separation. Such phase separation is readily achieved because of the relative immiscibility of the hydrofluorocarbon (or chlorofluorocarbon or hydrochlorofluorocarbon) and hydrogen fluoride.

Contrary to the ready immiscibility of the older prior art halocarbons with hydrogen fluoride, some of the new "third generation" hydrofluorocarbons have proven to be highly or completely miscible with hydrogen fluoride, i.e., 1,1,1,3,3-pentafluoropropane) and practical phase separation does not occur.

It has been recognized that the selective extraction of one component of a mixture of halocarbon and hydrogen fluoride may be carried out using a solvent capable of such selective extraction. However, the new "third generation" hydrofluorocarbons have been found to be partly or completely miscible with such solvent/hydrogen fluoride mixtures making such selective extraction very difficult or impossible.

Numerous normally effective separations additives, i.e., 4-chlorotoluene, pentachloropropane, tetramethylamine fluoride, etc. have been shown to be completely ineffective in causing any phase separation in saturated fluorinated aliphatic hydrocarbon/hydrogen fluoride systems.

In the aforementioned U.S. Pat. No. 5,616,819 sodium fluoride, potassium fluoride and ammonium fluoride are disclosed as effective in causing phase separation when added to fluorocarbon/hydrogen fluoride mixtures. Each is, however, susceptible to technical problems in large scale applications Accordingly, there is a need for having available methods and compositions to carry out such methods to achieve phase separation of hydrofluorocarbon/hydrogen fluoride mixtures.

SUMMARY OF THE INVENTION

It has now been discovered that a number of chemical compounds of various functional types can separate hydrogen fluoride from saturated fluorinated aliphatic hydrocarbons. These compounds include the alkanolamines, benzene substituted with halo, trifluoromethyl or $C_1$ to $C_6$ alkyl and solutions of sulfuric acid optionally containing one or more alkali metal salts.

DESCRIPTION OF THE PREFERRED EMBODIMENTS

The alkanolamine phase separation additives of the present invention are from a family of compounds that are normally used for the extraction (or scrubbing) of CO, $CO_2$, $SO_2$ and $H_2S$ from flue gases and not for phase separation or acid removal. They have the formula

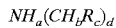

where R is $C_1$ to C6 linear or branched alkylene substituted with at least one hydroxy group, wherein a and d is 0 or the integers 1 or 2 and a+d=3 and b is 0 or the integer 1 or 2 and b+c=3.

In the above alkanolamine phase separation additives, it is preferred that R is $C_1$ to $C_4$ alkylene substituted with one hydroxy group such as hydroxymethylene, hydroxyethylene hydroxypropylene and the like and that b is 1 or 2. Most preferably, the group —$CH_bR_c$ is 2-hydroxyethyl, 1-methyl-2-hydroxyethyl and d is 1,2 or 3.

While not wishing to be bound by the following theory, it appears that the alkanolamines such as ethanolamine and diethanolamine sequester hydrogen fluoride as an assumed complex and liberate the hydrofluorocarbon.

In the process of the present invention, alkanolamine concentrations from about 5.0% to about 50.0% by weight based on the weight of saturated fluorinated hydrocarbon have been shown to be effective. Preferably from about 5.0% to about 20.0% by weight most preferably from about 5.0% to about 10.0% based on weight of saturated fluorinated aliphatic hydrocarbon are used in the process of the present invention.

Recoveries of the hydrofluorocarbon are high, typically greater than 80%, and residual hydrogen fluoride levels in the hydrofluorocarbon liquid are low, i.e., less than 1%. Significantly, hydrogen fluoride can be easily recovered from the hydrogen fluoride/alkanolamine solution by distilling the hydrogen fluoride from the alkanolamine, making recycle of both the hydrogen fluoride and the alkanolamine an uncomplicated procedure.

Other effective additives useful in separating hydrogen fluoride from hydrochlorocarbons are certain aromatic and haloaromatic compounds. These compounds are $C_6$ to $C_{10}$ aryl, for example phenyl or naphthyl, unsubstituted or substituted with at least one $C_1$ to $C_6$ alkyl, for example methyl, ethyl, etc., halo, for example chloro, ortho, meta or para dichloro, fluoro, etc., or at least one halo-substituted $C_1$ to $C_6$ alkyl, for example trifluoromethyl. It is believed that whereas the alkanolamines operate by selectively solvating the hydrogen fluoride, the aromatic and haloaromatic compounds operate by selectively solvating the hydrofluorocarbon. The haloaromatic compounds, such as chlorobenzene are particularly effective in this respect.

Other phase separation compounds that are also effective according to the method of the present invention are sulfuric acid, i.e. 100% $H_2SO_4$ (1.8305 specific gravity), aqueous solutions of sulfuric acid, i.e. <100% $H_2SO_4$ (specific gravity from about 1.830 to about 1.0051) or aqueous solutions of sulfuric acid admixed with at least one alkali metal sulfate.

When sulfuric acid and alkali metal sulfate admixtures are used, it is preferred that they are 1 to 1 mixtures. However mixtures of sulfuric acid with alkali metal sulfates can range from 100 parts of sulfuric acid to 1 part of alkali metal sulfate to 1 part of sulfuric acid to 100 parts of alkali metal sulfate. Aqueous solutions of these mixtures are useful in this embodiment of the present invention when mixed at admixture concentrations of as little as about 1 % water (with 99% of the admixture) to as much as about 99% water (with 1% of the admixture).

These compounds or mixtures of compounds are used in the same manner as the alkanolamines discussed earlier.

In the Examples below, the compound HFC-245fa is 1,1,1,3,3-pentafluoropropane. The compound "HF" is anhydrous hydrogen fluoride.

EXAMPLE 1
Separation of Hydrogen Fluoride from HFC 245fa-Alkanolamine extraction A 100 mL PTFE separatory funnel was charged with 12.2 g (0.2 mol) of ethanolamine. 40.8 g (2.0 mol) of HF was added with mixing. The amine*HF mixture was cooled to 0° C. and 42.1 g (0.31 mol) of HFC-245fa was added. The separatory funnel was sealed and the contents warmed to room temperature. The contents were then thoroughly mixed by shaking and allowed to stand one minute. The lower (organic) layer was drained into crushed ice and weighed. The resultant organic/water mixture was titrated with 0.25N sodium hydroxide (NaOH) solution.

| Additive | % 245fa recovered | % HF w/w in rec'd 245fa |
|---|---|---|
| Ethanolamine | 88% | 0.48% |
| Diethanolamine | 83 | 0.46 |
| Triethanolamine | 74 | 0.63 |
| 2-(Methylamino) | 63 | 0.16 |
| 2-Amino-2-methyl-1-propanol | 71 | 0.48 |
| 2-Amino-2-methyl-1,3-propanediol | 83 | 0.50 |
| Tris(hydroxymethyl aminomethane | 85 | 0.90 |
| Ethylene glycol | 27 | 1.50 |
| Water | 56 | — |
| $Me_4NF$ | m | — |
| $Me_4NF/NaHF_2$ | 24 | — |
| $Me_3HNF$ | m | — | m = miscible

EXAMPLE 2
Separation of HF from HFC-245fa - Sulfuric acid and its alkali metal salts extraction A 100 mL PTFE separatory funnel was charged with 3.9 grams of $KHSO_4$. 11.1 grams of concentrated sulfuric acid was added. The mixture was cooled to 0° C. and 6 grams of HF was slowly added, followed by 9 grams of HFC-245fa. The separatory funnel was sealed and the contents warmed to room temperature. The contents were then thoroughly mixed by agitation of the separatory funnel and allowed to stand for one minute. The lower (acid) layer was drained from the separatory funnel and weighed. The upper (organic) layer was subsequently drained into crushed ice and weighed. The resultant organic/water mixture was titrated with a 0.25 N NaOH solution. The results are as follows:

| Additive | % HFC245fa Recovered | % HF w/w in Recovered HFC245fa |
|---|---|---|
| $H_2SO_4/KHSO_4$ | 72 | 0.4(total acid as HF) |
| $H_2SO_4$ | 100 | 22.8 |

(28% w/w $H_2SO_4$ extracted 53% of HF mixture)

EXAMPLE 3
Separation of HF from HFC-245fa - Halogen-substituted aromatic hydrocarbon extraction A 100 mL PTFE separatory funnel was charged with 10.4 g of chlorobenzene. 11 g of HFC-245fa was added with mixing. The 245fa/PhCl mixture was cooled to 0° C. and 5.9 g of HF was slowly added. The separatory funnel was sealed and the contents warmed to room temperature. The contents were then thoroughly mixed by shaking and allowed to stand one minute. The lower (organic) layer was drained into crushed ice and weighed. The resultant organic/water mixture was titrated with 0.25N NaOH solution.

| Additive | % 245fa recovered | % HF w/w in rec'd 245fa |
|---|---|---|
| Chlorobenzene | 68 | 3.5 |
| 1,2-Dichloro benzene | 0 | — |
| 4-Chlorotoluene | 0 | — |
| Trifluoromethyl benzene | 60 | — |

EXAMPLE 4
Separation of HF from HFC-245fa - Aromatic hydrocarbon extraction

A 100 mL PTFE separatory funnel was charged with 49 g of cold toluene. 51 g of HFC-245fa was added. The 245fa/toluene mixture was cooled to 0° C. and 49 g of HF was slowly added. The separatory funnel was sealed and the contents warmed to room temperature. The contents were then thoroughly mixed by shaking and allowed to stand one minute. The lower (HF) layer was drained onto crushed ice and the retained 245fa separated and weighed. The upper (organic) layer was subsequently drained into crushed ice and weighed. The resultant organic/water mixture was titrated with 0.25N NaOH solution.

| Additive | % 245fa recovered | % HF w/w in rec'd 245fa |
|---|---|---|
| Toluene | 54 | 8.3 |
| Nitrobenzene | m | — | m = miscible

I claim:

1. A method of separating a mixture of at least one hydrofluorocarbon and hydrogen fluoride comprising treating said mixture with a compound selected from the group consisting of an alkanolamine of the formula $$NH_a(CH_bR_c)_d$$

where R is $C_1$ to $C_6$ linear or branched alkylene substituted with at least one hydroxy group. wherein a and d are the integers 1 or 2 and a+d=3 and b is 0 or the integer 1 or 2 and b+c=3, $C_6$ to $C_{10}$aryl unsubstituted or substituted with halo or halo-substituted $C_1$ to $C_6$ alkyl, and sulfuric acid admixed with at least one alkali metal sulfate; and separating from said treated mixture said at least one hydrofluorocarbon.

2. The method according to claim 1 wherein said compound is an alkanolamine $$NH_a(CH_bR_c)d$$

where R is $C_1$ to $C_6$ linear or branched alkylene substituted with at least one hydroxy group, wherein a and d are the integers 1 or 2 and a+d=3 and b is 0 or the integer 1 or 2 and b+c=3.

3. The method according to claim 2 wherein R is $C_1$ to $C_4$ alkylene substituted with one hydroxy group and b is 1 or 2.

4. The method according to claim 3 wherein the group —$CH_bR_c$ is 2-hydroxyethyl, 1-methyl-2-hydroxyethyl and c is 1,2 or 3.

5. The method according to claim 1 wherein said compound is $C_6$ to $C_{10}$ aryl unsubstituted or substituted with halo or halo-substituted $C_1$ to $C_6$ alkyl.

6. The method according to claim 5 wherein said compound is $C_6$ to $C_{10}$ aryl substituted with halo-substituted $C_1$ to $C_6$ alkyl.

7. The method according to claim 6 wherein said compound is $C_6$ to $C_{10}$ aryl substituted with trifluoromethyl.

8. The method according to claim 6 wherein said compound is $C_6$ to $C_{10}$ aryl substituted with chloro.

9. The method according to claim 1 wherein said compound is sulfuric acid admixed with at least one alkali metal sulfate.

10. The method according to claim 9 wherein said admixture comprises sulfuric acid and potassium bisulfate.

11. The method according to claim 10 wherein said admixture comprises sulfuric acid and potassium bisulfate in a ratio of 1 to 1.

\* \* \* \* \*